US00PP12209P2

(12) United States Plant Patent
Colfer

(10) Patent No.: US PP12,209 P2
(45) Date of Patent: Nov. 20, 2001

(54) ARTICHOKE PLANT NAMED 'PS-MSG0290'

(75) Inventor: William J. Colfer, Aptos, CA (US)

(73) Assignee: Seed Research Services, LLC, Salinas, CA (US)

( * ) Notice: Subject to any disclaimer, the term of this patent is extended or adjusted under 35 U.S.C. 154(b) by 0 days.

(21) Appl. No.: 09/482,568

(22) Filed: Jan. 14, 2000

(51) Int. Cl.[7] ..... A01H 5/00

(52) U.S. Cl. ..... Plt./258

(58) Field of Search ..... Plt./258

(56) References Cited

U.S. PATENT DOCUMENTS

P.P. 2,738 * 5/1967 Montgomery et al. ..... Plt./258

* cited by examiner

*Primary Examiner*—Bruce R. Campell
*Assistant Examiner*—Wendy C Baker
(74) *Attorney, Agent, or Firm*—Foley & Lardner

(57) ABSTRACT

A new and distinct cultivar of Artichoke plant named 'PS-MSG0290' characterized by having male sterility which is demonstrated by the absence of pollen on all florets during anthesis. The new cultivar has numerous, large, non-glossy heads and thick, fleshy bracts and hearts. 'PS-MSG0290' shows uniformity of head shapes and a compact, reduced plant growth habit.

3 Drawing Sheets

BACKGROUND OF THE INVENTION

The present invention comprises a new and distinct cultivar of artichoke plant, botanically know as *Cynara scolymus L.* and herein referred to by the cultivar name 'PS-MSG0290'.

*Cynara scolymus L.,* commonly known as Globe artichoke, is a thistle-like perennial herb and is a member of the family Asteraceae. Globe artichokes comprise leaves which are pinnately lobed but primarily spineless, globose capitula composed of overlapping layers of large involucral bracts, and receptacles which are enlarged and fleshy. Globe artichoke plants may be propagated by division and are essentially grown for the production of the immature flower heads, which are considered as vegetable delicacies. Fresh artichokes may be steamed or boiled, after which the fleshy receptacle, inner and outer bracts, and parts of the floral stem may be eaten.

The new cultivar is a product of a planned breeding program carried out by the inventor, William J. Colfer, in Chowchilla, Calif. in 1996. 'PS-MSG0290' was discovered and selected within the progeny of open-pollinated proprietary cultivar GGMSC6 by the inventor, William J. Colfer.

Asexual reproduction of the new cultivar by division was performed by the inventor in Watsonville, Calif. in 1997, and has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be basic characteristics of 'PS-MSG0290' which in combination distinguish this Artichoke as a new and distinct cultivar:

1. Male sterility which is demonstrated by the absence of pollen on all florets during anthesis;
2. Numerous, large, non-glossy heads;
3. Thick, fleshy bracts and hearts;

4. Uniformity of head shapes; and
5. Compact, reduced plant growth habit.

'PS-MSG0290' has not been observed under all possible environmental conditions. The phenotype of the new cultivar may vary with variations in environment such as temperature, humidity, light intensity and daylength, without any change in the genotype. The following observations, measurements and values describe the new cultivar as grown in Chowchilla, Calif. under conditions which closely approximate those generally used in horticultural practice.

Chowchilla is located in California's central San Juaquin valley. Conditions can vary greatly during the summer months. Air temperatures can range between the low 60's (F.) to temperatures well over 100° F. Relative humidity is generally low with values ranging from the mid 40's to the high 60's. Prevailing winds are westerly and rainfall averages rarely exceed 15" (inches) of rainfall.

In the following description, holding quality was measured by the physical appearance of the head. This includes the head's appearance following 3, 7, and 10-day storage periods in cold storage at 34° F. The head's exterior (oxidation) was observed at each of the three observation points. Browning and blackening of plant tissue was evaluated as light, moderate and extreme. Juiciness was measured by observing visible exudate and rated as absent, moderate-presence or excess. Overall storage response was measured by observing heads following 3, 7 and 10-day cold storage periods. These observations concentrated on visible color variability and/or presence of lesions or other cosmetic anomalies. Leaf ratio (L/W) was determined by dividing representative leaf sample lengths by their width. Finally, head response (weather) was determined by observing the heads at maturity. These field observations focus on the presence or absence of bronzing, necrotic or chlorotic lesions or any abiotic responses to environmental conditions. AFLP (DNA analysis) was conducted on each parental selection.

BRIEF DESCRIPTION OF THE DRAWINGS

The accompanying color photographic illustrations show typical fruit and foliage characteristics of a specimen plant of 'PS-MSG0290', with colors being as true as possible with illustrations of this type.

The first drawing is a side elevational view of the fruit and foliage.

The second drawing is a close-up view of the fruit showing its physical dimension.

The third drawing is close-up view showing a vertical cross-section of the fruit.

DETAILED BOTANICAL DESCRIPTION

The following observations, measurements, and values describe the new cultivar as grown in Chowchilla, Calif. The data was collected from first year tissue culture outplants. Selections were made in outdoor field settings. Plants are grown in the soil in rows. Row spacing (bed centers) in 38 inches, individual plant spacing varies between 12–36 inches, depending upon original seed germination. Stem segments were used to develop Shoots which were transferred to a rooting medium for root development. These plants were then transplanted into the greenhouse for final plant growth and development. The date of first harvest is approximately May 20 and the date of final harvest is approximately June 20.

Color references are measured against The Munsell Book of Color, Munsell Color Macbeth Division of Kollmorgen Corporation.

Parentage: 'PS-MSG0290' was discovered and selected within the progeny of open-pollinated proprietary cultivar GGMSC6.

Classification: *Cynara scolymus L.* c.v. 'PS-MSG0290'.

Propagation: Asexual production either by tissue culture using stem segments to develop shoots for root development of division.

Plant:

*Height*.—Approximately 60.69–88.90 cm.

*Width*.—Approximately 135.89–187.33 cm.

*Form*.—Full.

*Growth habit*.—Upright.

*Plant vigor*.—10.0 cm (2–3 leaves)–125 cm (60–68 leaves) from fall planting (mid October) to final harvest (following May).

*Side shoots*.—Number: Approximately 2–4. Development: Moderate. Length: 59.0–112.5 cm, average 88.40. Diameter: 15.0 mm–27.0 mm, average 20.0 mm. Color: Pubescence with color range: 10Y 9/2–5GY 9/2; with distinct anthocyanin coloration, color range: 7.5R 5/4–7.5R 4/4.

*Main stem*.—Length: 24.0–28.0 cm, average 25.90 cm. Diameter: 27.0–37.0 mm, average 33.40 mm. Color: Highly pubescent, color range: 10Y 9/2–5GY 9/2; some lower stem anthocyanin coloration, color range: 7.5R 5/4–7.5R 4/4. Leaves on Main Stem: Approximately 13–22, average 17.33 leaves.

*Foliage density*.—Moderate; increased by side-shoot development and number.

Capitulum:

*Size*.—Primary: Approximately 38.74–40.64 cm. Secondary: Approximately 31.12–35.56 cm.

*Shape*.—Oval to oval-spherical; predominantly oval-shaped.

*Number*.—Approximately 3–7 per plant.

*Texture*.—Intermediate, smooth.

*Fragrance*.—Mild.

*Bract size*.—Length: Approximately 6.7–7.9 cm. Width: Approximately 5.0–6.3 cm.

*Bract shape*.—Predominantly oval-shaped; some range is observed including obovate shapes.

*Bract texture*.—Smooth, slight texture.

*Bract number*.—Approximately 38–50 per head.

*Bract color*.—Inner: 2.5 GY 9/2–2.5 GY 9/4. Outer: 2.5 GY 9/6.

*Bract firmness*.—Firm, thick, fleshy and well attached.

*Bract basal thickness*.—Approximately 4.0–7.0 mm.

*Heart description*.—Concave and full with a well developed shoulder.

*Heart color*.—10 Y 9/2–7.5 Y 9/2 .

*Pappus length*.—Approximately 1.4–1.6 cm.

*Pappus color*.—Variable white/yellow coloration, color range: 5Y 9/2–7.5Y 9/2–10Y 9/2.

*Overall cold storage response*.—Good; some regions that were damaged during harvest displayed some browning.

*Head firmness*.—Firm, heads (capitula) are dense.

*Gloss*.—Dull, no sheen or glossiness visible.

*Cold storage* (*hold quality*).—Good; heads remain dense and free of decay.

*Head exterior* (*oxidation*).—Moderate response; some tissue is slightly browned not blackened.

*Juiciness*.—Moderately present; some exudate is visible, but no excess volumes observed.

*Head response* (*weather*).—No adverse responses to weather conditions were observed on heads (capitula) or other plant tissues.

*Bud burst*.—Apr. 5–Apr. 10.

*Bloom time*.—Approximately May 10.

*Duration of bloom*.—Approximately 37–40 days.

*Bloom diameter*.—7.62–13.34 cm; average 10.56 cm.

*Bloom depth*.—8.89–11.43 cm; average 10.10 cm.

*Bloom shape*.—Head.

*Florets*.—1063–1203 florets per head, average 1132 florets per head.

*Bud weight*.—Primary bud weight 450.75–470.1 grams, average 460.85 grams; secondary bud weight 425.6–460.1 grams, average 437.17 grams.

Foliage:

*Shape*.—Long strap-like leaves characterized by lobes that extend nearly to the midvein, lobes are reduced, mildly dentate.

*Length*.—Approximately 78.3–105.4 cm.

*Width*.—Approximately 47.3–70.4 cm.

*Leaf serrations*.—Approximately 7.56–12.23 cm.

*Leaf basal angle*.—Approximately 20–40 degrees.

*Leaf ratio* (*L/W*).—Approximately 1.5–2.06.

*Leaf area*.—Approximately 4347.42–7388.54 $cm^2$.

*Upper leaf surface color*.—Color range: 7.5GY 4/4–7.5GY 4/6–7.5GY 5/8.

*Lower leaf surface color*.—Extreme pubescence, color range: 7.5GY 7/2–7.5 GY 6/2–7.5GY 6/4.

*Texture*.—Slightly textured becoming reduced as the leaves mature.

*Venation*.—Indistinct, blends; med-vein is prominent and white to palegreen, pubescence with color range 5GY 6/6–5GY 5/6; leaf lobes are green and indistinct.

*Pubescence*.—Sparse; upper leaf surface is sparse, but lower leaf surface's pubescence is visible along petiole and leaf lobes.

*Leaf basal thickness*.—Approximately 11.0–17.0 mm.

*Leaf distance between serrations*.—Approximately 4.0–6.0 cm.

*Petiole length*.—Approximately 8.0–12.0 cm.

*Petiole width*.—Approximately 3.2–5.0 cm.

*Petiole color*.—Color range: 5GY 6/6–5/6 with subtle anthocyanin coloration color range: 7.5R 5/4–7.5R 4/4.

Seeds:

*Shape*.—Ovate with some asymmetrical mid-section dimensions.

*Number*.—12–501 seeds per head; average 201 seeds per head.

*Length*.—8.0–9.0 mm; average 8.67 mm.

*Width*.—3.5–5.0 mm; average 4.06 mm.

*Color*.—Tan, some light brown coloration, with speckled pattern.

Plant bud disease resistance susceptibility: Moderate infection of powdery Mildew, *Leveillula taurica*, Ramularia ssp. and Alternaria spp. leaf spot were noted; infection was observed throughout the plant's canopy.

General observations: 'PS-MSG0290' is male sterile lacking pollen on all florets during anthesis (flowering). 'PS-MSG0290' plants have moderate height ranging from 60–88 cm. Compared to the head qualities of artichoke variety Green Globe, 'PS-MSG0290' has thicker fleshy bracts, thicker fleshy hearts (receptacles), oval shape and green (non-glossy) exterior coloration. These non-glossy heads (capitula) are large. 'PS-MSG0290' produces an average size (12) primary, size (18) secondary and size (24–36) tertiaries. Head numbers range between 3–7 heads per plant. Anthocyanin coloration is visible on both interior bracts and exterior lower bracts, color range 7.5R 5/4–7.5R 4/4. The head spinosity is moderate with average spine length of approximately 1–3 mm. The plants upright growth habit is compact, but vigorous. The canopies' coloration is a medium green/yellow color ranging from medium to darker shades. These colors range on the Munsell Leaf Color Chart 5 GY 4/4–5 GY 4/6. Leaf spinosity is moderate, categorized as few. Floral stalk development during anthesis produces a purple flower, color range at bloom 10P 5/2–10P 4/12–10P 4/10.

I claim:

1. A new and distinct cultivar of Artichoke plant named 'PS-MSG0290', as described and illustrated.

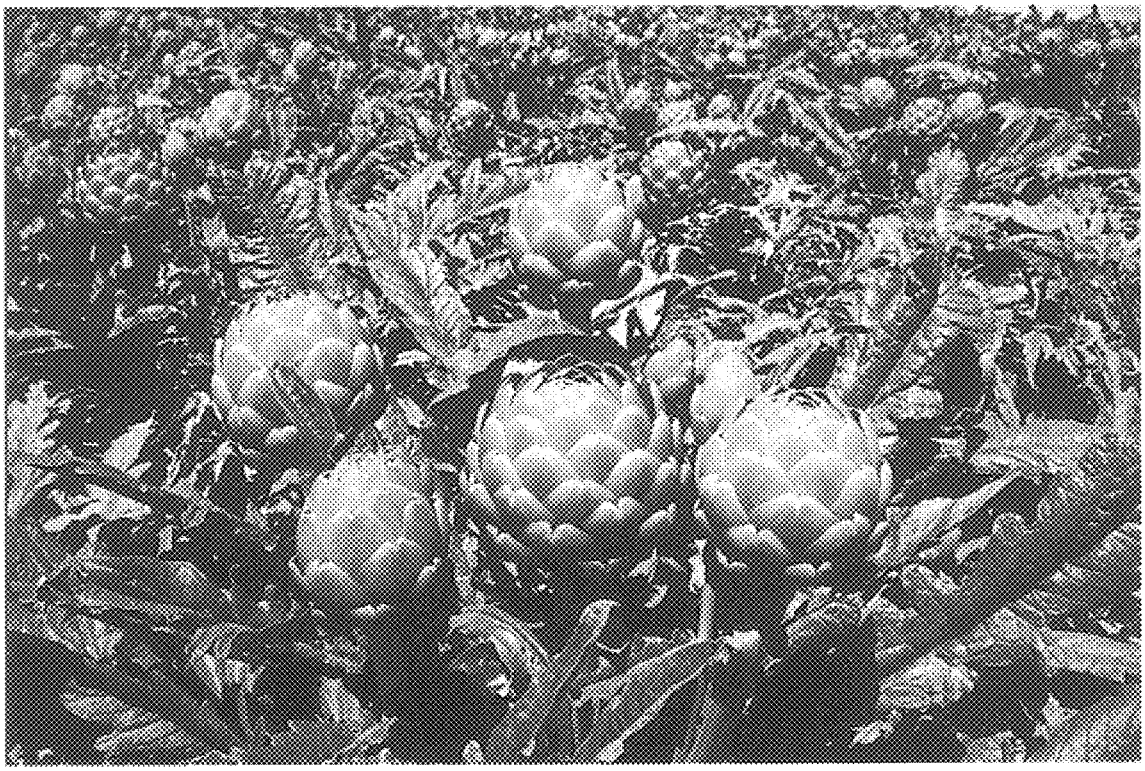

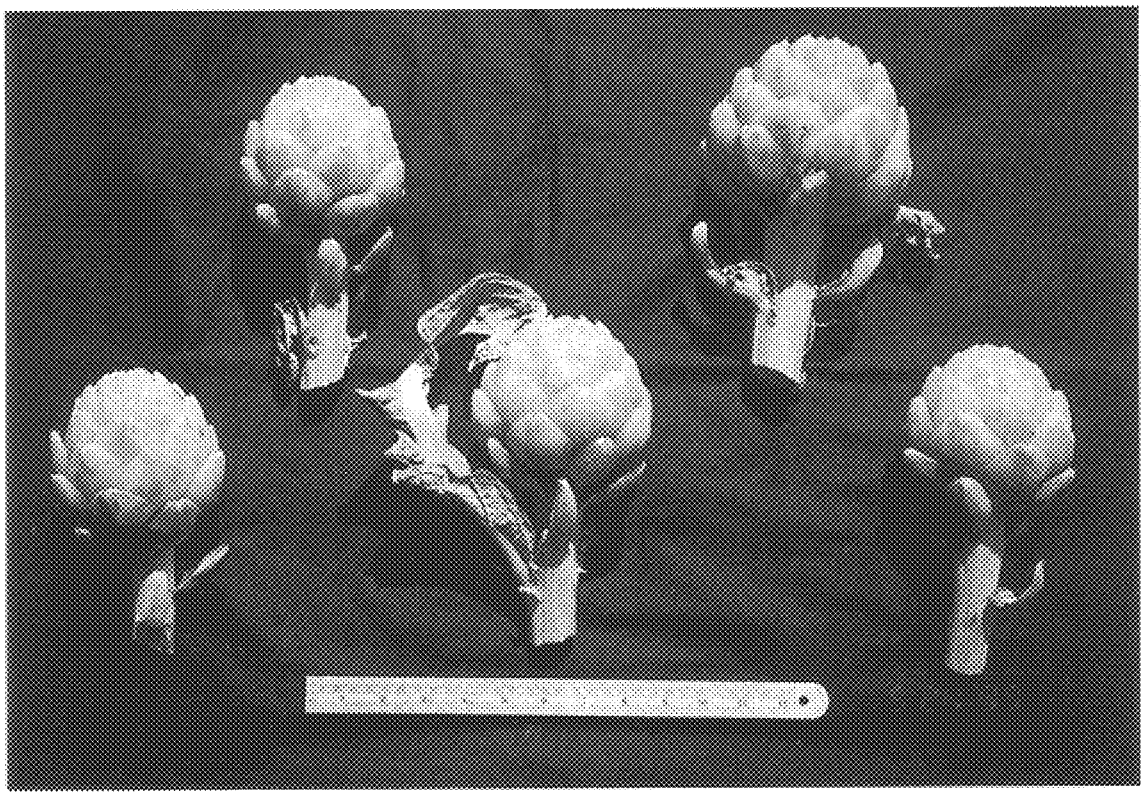

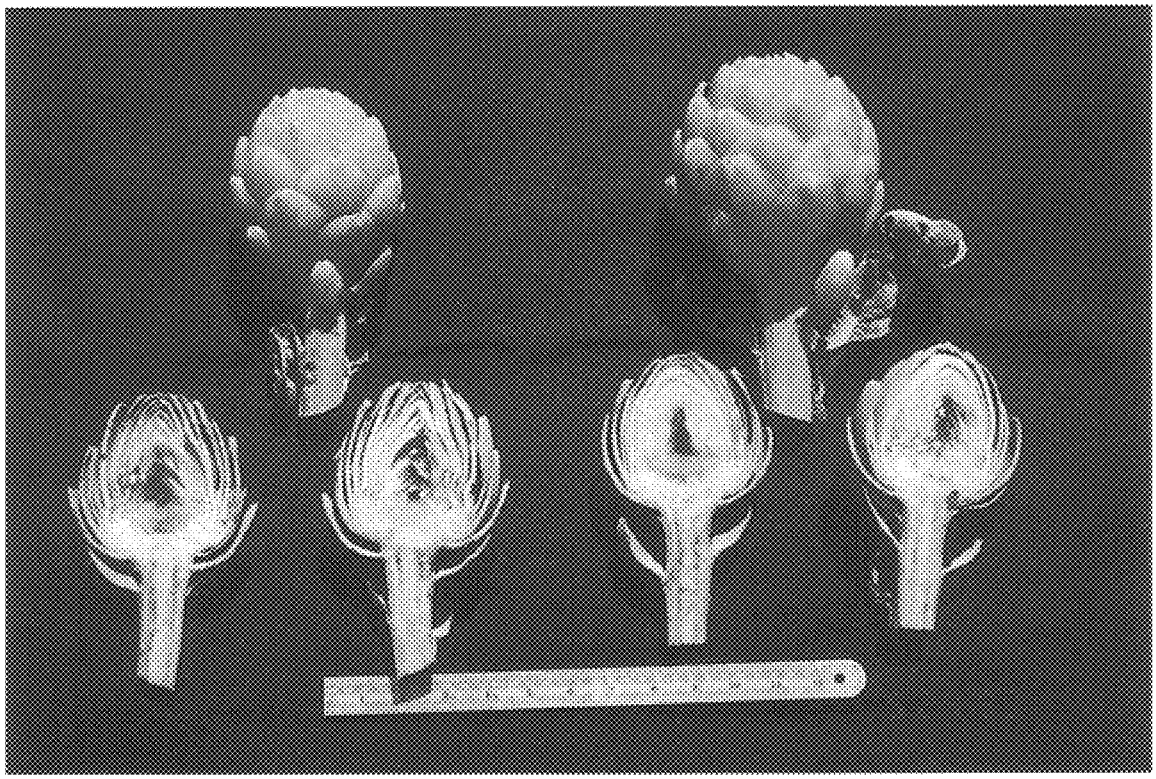

* * * * *